(12) United States Patent
Osawa et al.

(10) Patent No.: US 10,422,695 B2
(45) Date of Patent: Sep. 24, 2019

(54) OPTICAL CHARACTERISTIC MEASUREMENT SYSTEM AND CALIBRATION METHOD FOR OPTICAL CHARACTERISTIC MEASUREMENT SYSTEM

(71) Applicant: Otsuka Electronics Co., Ltd., Osaka (JP)

(72) Inventors: Yoshihiro Osawa, Moriyama (JP); Tsutomu Mizuguchi, Ritto (JP); Munehiro Noguchi, Kusatsu (JP)

(73) Assignee: Otsuka Electronics Co., Ltd., Osaka (JP)

( * ) Notice: Subject to any disclaimer, the term of this patent is extended or adjusted under 35 U.S.C. 154(b) by 0 days.

(21) Appl. No.: 16/271,621

(22) Filed: Feb. 8, 2019

(65) Prior Publication Data

US 2019/0170578 A1    Jun. 6, 2019

Related U.S. Application Data

(62) Division of application No. 15/200,535, filed on Jul. 1, 2016, now Pat. No. 10,222,261.

(30) Foreign Application Priority Data

Jul. 7, 2015   (JP) .................. 2015-136036

(51) Int. Cl.
*G01J 3/28*   (2006.01)
*G01J 3/18*   (2006.01)
(Continued)

(52) U.S. Cl.
CPC ............... *G01J 3/28* (2013.01); *G01J 3/0218* (2013.01); *G01J 3/0251* (2013.01);
(Continued)

(58) Field of Classification Search
CPC ... G01J 1/0252; G01J 3/0286; G01N 21/0332
See application file for complete search history.

(56) References Cited

U.S. PATENT DOCUMENTS 5,953,118 A   9/1999  O'Rourke et al.
6,075,595 A   6/2000  Malinen
(Continued)

FOREIGN PATENT DOCUMENTS

JP   H09-159604 A   6/1997
JP   H09-292281 A   11/1997
(Continued)

OTHER PUBLICATIONS

An Office Action; "Notice of Grounds of Rejection," issued by the Japanese Patent Office dated Mar. 26, 2019, which corresponds to Japanese Patent Application No. 2015-136036 and is related to U.S. Appl. No. 16/271,621; with English language translation.
(Continued)

*Primary Examiner* — Kenneth J Malkowski
(74) *Attorney, Agent, or Firm* — Studebaker & Brackett PC

(57) ABSTRACT

There is provided an optical characteristic measurement system that can be set up in a relatively short time and can increase a detection sensitivity. The optical characteristic measurement system includes a first measurement apparatus. The first measurement apparatus includes: a first detection element arranged in a housing; a first cooling unit at least partially joined to the first detection element that cools the detection element; and a suppression mechanism that suppresses temperature variations occurring around the detection element in the housing.

5 Claims, 10 Drawing Sheets

(51) Int. Cl.
*G01N 21/27* (2006.01)
*G01J 3/02* (2006.01)
*G01N 21/64* (2006.01)
*G01N 21/33* (2006.01)
*G01N 21/35* (2014.01)
*G01N 21/03* (2006.01)

(52) U.S. Cl.
CPC ............ *G01J 3/0254* (2013.01); *G01J 3/0286* (2013.01); *G01J 3/18* (2013.01); *G01N 21/274* (2013.01); *G01N 21/33* (2013.01); *G01N 21/35* (2013.01); *G01N 21/645* (2013.01); *G01N 21/0332* (2013.01); *G01N 2201/1211* (2013.01)

(56) References Cited

U.S. PATENT DOCUMENTS

| | | | | |
|---|---|---|---|---|
| 7,034,935 | B1* | 4/2006 | Kruzelecky | ............... G01J 3/02 250/339.02 |
| 2004/0141676 | A1 | 7/2004 | Bugaud et al. | |
| 2011/0155926 | A1 | 6/2011 | Ohkubo | |
| 2011/0226961 | A1* | 9/2011 | Osawa | ............... G01J 1/58 250/458.1 |
| 2012/0249865 | A1 | 10/2012 | Ichikawa | |
| 2014/0063496 | A1* | 3/2014 | Owa | ............... G01J 3/0286 356/319 |
| 2016/0109669 | A1 | 4/2016 | Moidu | |

FOREIGN PATENT DOCUMENTS

| | | |
|---|---|---|
| JP | H9-297111 A | 11/1997 |
| JP | 2003-283174 A | 10/2003 |
| JP | 2004-523764 A | 8/2004 |
| JP | 2011-196735 A | 10/2011 |
| JP | 2012-212976 A | 11/2012 |
| JP | 2014-048176 A | 3/2014 |
| WO | 2010/084566 A1 | 7/2010 |

OTHER PUBLICATIONS

An Office Action; "Decision for Rejection," issued by the Japanese Patent Office on Jun. 11, 2019, which corresponds to Japanese Patent Application No. 2015-136036 and is related to U.S. Appl. No. 16/271,621; with English language translation.

* cited by examiner

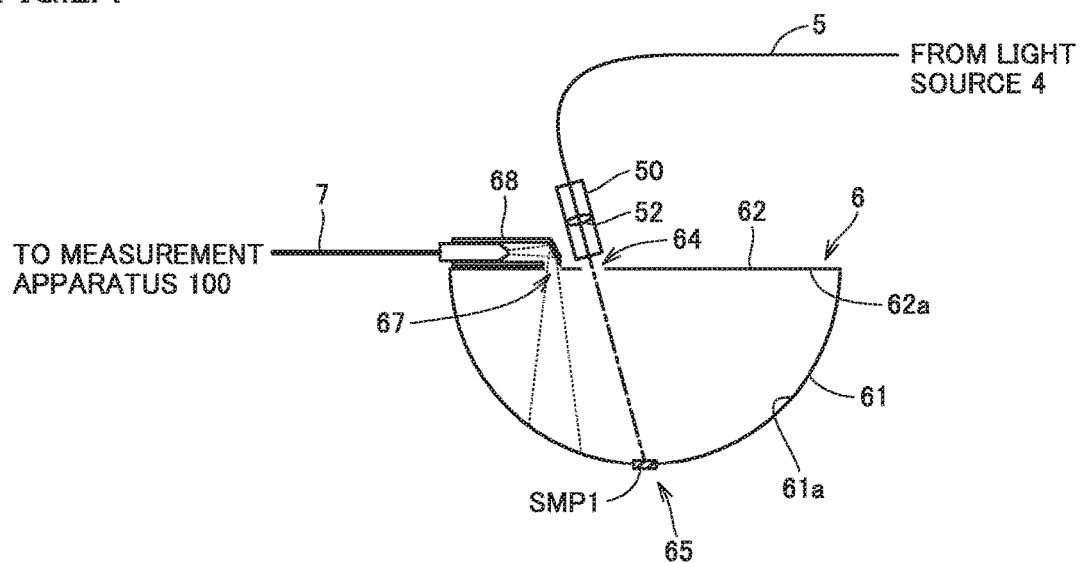
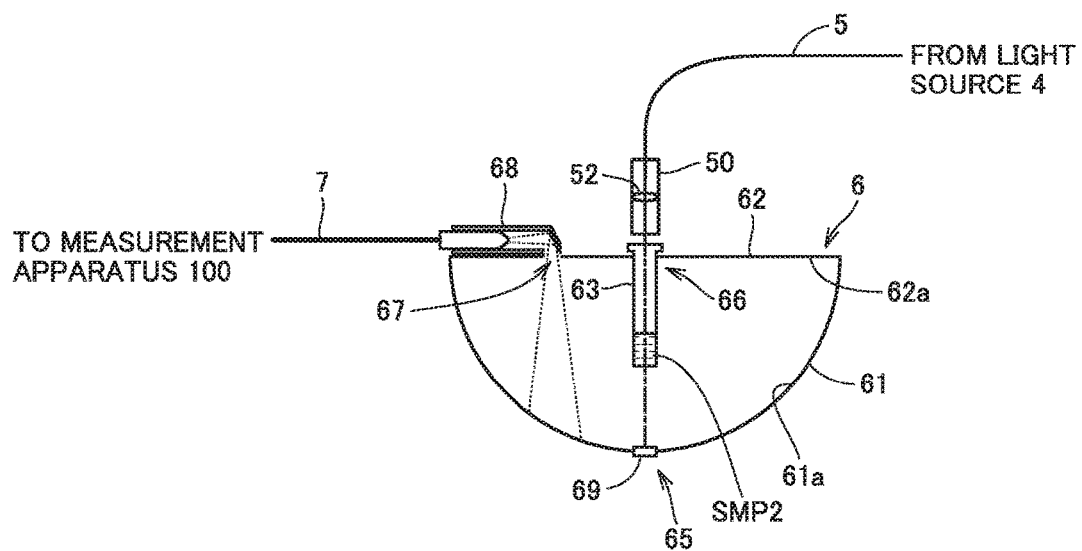

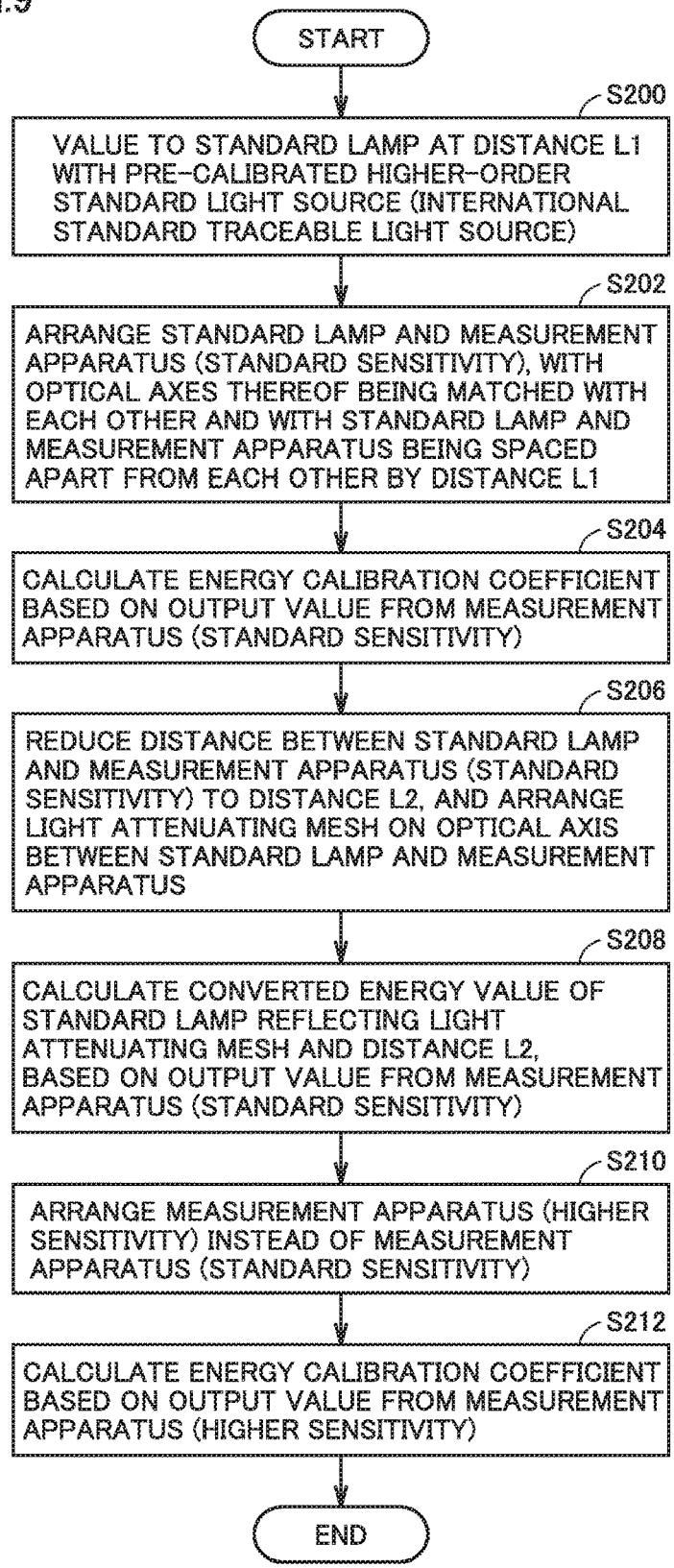

OPTICAL CHARACTERISTIC MEASUREMENT SYSTEM AND CALIBRATION METHOD FOR OPTICAL CHARACTERISTIC MEASUREMENT SYSTEM

CROSS-REFERENCE TO RELATED APPLICATIONS

This application is a divisional of U.S. application Ser. No. 15/200,535 filed Jul. 1, 2016 and claims priority to Japanese Patent Application No. 2015-136036 filed Jul. 7, 2015, the disclosure of which is incorporated by reference herein.

BACKGROUND OF THE INVENTION

Field of the Invention

The present technique relates to an optical characteristic measurement system that can measure optical characteristics, and a calibration method for the optical characteristic measurement system.

Description of the Background Art

There is a need for measuring the feeble light emitted by a photosensitizing substance in order to evaluate characteristics of a material or a reagent including the substance. For example, Japanese Patent Laying-Open No. 09-159604 discloses a singlet oxygen measurement apparatus that can measure even a sample including a photosensitizing substance having a light absorption characteristic with respect to an arbitrary wavelength in a range of an ultraviolet region to a visible region, and a sample that is directly and indirectly unstable with respect to the light and available only in a small amount.

In addition, Japanese Patent Laying-Open No. 09-292281, International Publication No. 2010/084566 and Japanese Patent Laying-Open No. 2011-196735 disclose a measurement apparatus and a measurement method for measuring the quantum efficiency indicating a ratio between an amount of photons absorbed by a sample including a fluorescent substance and an amount of photons of fluorescence generated from the sample.

In the singlet oxygen measurement apparatus disclosed in Japanese Patent Laying-Open No. 09-159604, a liquid nitrogen cooling-type germanium detector is used to increase a detection sensitivity. By cooling a detection element with liquid nitrogen or the like, the detection element can be stabilized and a detection dynamic range can be enlarged. On the other hand, in order to cool the detection element with liquid nitrogen, a few hours preparation including precooling and the like is required before the actually usable state is achieved, and thus, this singlet oxygen measurement apparatus is not practical.

SUMMARY OF THE INVENTION

There is a demand for realizing an optical characteristic measurement system that can be set up in a relatively short time and can increase a detection sensitivity.

According to an aspect of the present invention, there is provided an optical characteristic measurement system including a first measurement apparatus. The first measurement apparatus includes: a first detection element arranged in a housing; a first cooling unit at least partially joined to the first detection element, for cooling the first detection element; and a suppression mechanism for suppressing temperature variations occurring around the first detection element in the housing.

Preferably, the suppression mechanism includes a second cooling unit at least partially joined to the housing, for transferring heat in the housing to outside the housing.

Preferably, the suppression mechanism includes a heat insulation mechanism arranged around the housing, for reducing heat entry into the housing from around the housing.

Preferably, the optical characteristic measurement system further includes a second measurement apparatus. The first measurement apparatus further includes a first diffraction grating arranged to correspond to the first detection element and configured to guide light in a first wavelength range to the first detection element. The second measurement apparatus includes: a second detection element arranged in a housing; and a second diffraction grating arranged to correspond to the second detection element and configured to guide light in a second wavelength range to the second detection element. The first detection element of the first measurement apparatus is configured to have a detection sensitivity higher than a detection sensitivity of the second detection element of the second measurement apparatus.

Preferably, the optical characteristic measurement system further includes a bifurcated fiber for bifurcating the light from an object to be measured and guiding the light to each of the first and second measurement apparatuses.

Preferably, the first measurement apparatus is configured to have the detection sensitivity to a wavelength component in a near-infrared region. The second measurement apparatus is configured to have the detection sensitivity to at least a part of wavelength components included in a range of an ultraviolet region to a visible region.

According to another aspect of the present invention, there is provided a calibration method for an optical characteristic measurement system including a first measurement apparatus and a second measurement apparatus configured to have a detection sensitivity lower than a detection sensitivity of the first measurement apparatus. The calibration method for the optical characteristic measurement system includes: arranging a light source preliminarily valued by an energy value and the second measurement apparatus in accordance with a first arrangement condition, and determining an energy calibration coefficient of the second measurement apparatus based on an output value obtained by receiving light from the light source at the second measurement apparatus; arranging the light source and the second measurement apparatus in accordance with a second arrangement condition, and determining a converted energy value of the light source corresponding to the second arrangement condition based on the output value obtained by receiving the light from the light source at the second measurement apparatus and the energy calibration coefficient of the second measurement apparatus; and arranging the light source and the first measurement apparatus in accordance with the second arrangement condition, and determining an energy calibration coefficient of the first measurement apparatus based on an output value obtained by receiving the light from the light source at the first measurement apparatus and the converted energy value of the light source corresponding to the second arrangement condition.

According to an embodiment of the present invention, there is provided an optical characteristic measurement system that can be set up in a relatively short time and can increase a detection sensitivity.

In addition, according to an embodiment of the present invention, there is provided a calibration method for an optical characteristic measurement system including a first measurement apparatus and a second measurement apparatus configured to have a detection sensitivity lower than a detection sensitivity of the first measurement apparatus.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 2A and 2B are diagrams for describing a method for measuring optical characteristics with the optical characteristic measurement system shown in FIG. 1.

FIG. 9 is a flowchart showing a procedure for performing calibration on the optical characteristic measurement system according to the present embodiment.

DESCRIPTION OF THE PREFERRED EMBODIMENTS

Figure 1:
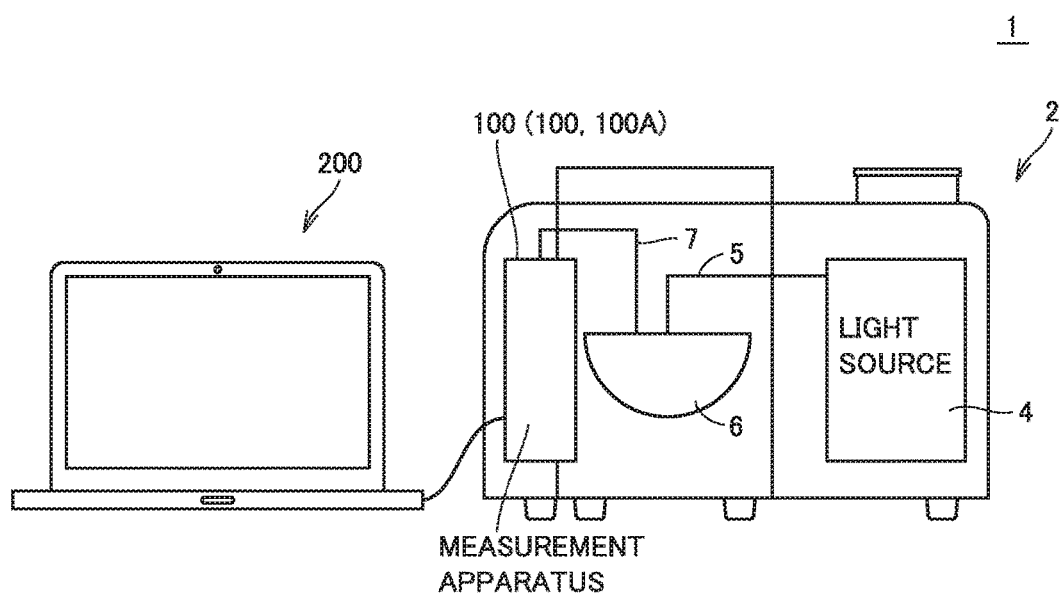
FIG. 1 is a schematic view showing a configuration example of an optical characteristic measurement system including an optical characteristic measurement apparatus according to the present embodiment.

An embodiment of the present invention will be described in detail with reference to the drawings. In the drawings, the same or corresponding portions are denoted by the same reference characters, and description thereof will not be repeated.

<A. System Configuration Example>

First, an optical characteristic measurement system 1 including an optical characteristic measurement apparatus (hereinafter also abbreviated as "measurement apparatus") according to the present embodiment will be described. FIG. 1 is a schematic view showing a configuration example of optical characteristic measurement system 1 including the optical characteristic measurement apparatus according to the present embodiment.

Referring to FIG. 1, optical characteristic measurement system 1 includes a light source 4, an integrator 6, a system main body 2 that houses a measurement apparatus 100, and a data processing apparatus 200. Although FIG. 1 shows the configuration example in which light source 4, integrator 6 and measurement apparatus 100 are housed in a single housing, the present invention is not limited thereto. A part of the components may be configured as a separate apparatus. In this case, only one or a plurality of measurement apparatuses 100 may form the optical characteristic measurement system.

Optical characteristic measurement system 1 shown in FIG. 1 can measure various optical characteristics. Examples of the optical characteristics include a total amount of light flux, an illuminance (or spectral irradiance), a brightness (or spectral radiance), a light intensity, color rendering (a chromaticity coordinate, an excitation purity, a correlated color temperature, and color rendering properties), an absorptivity, a transmittance, a reflectance, an emission spectrum (and a peak wavelength and a half-wave value), an excitation spectrum, external quantum efficiency (or external quantum yield), internal quantum efficiency (or internal quantum yield) and the like.

In the following description, the case of applying the excitation light of a prescribed wavelength (typically, the light in a range of the ultraviolet region to the visible region) to a sample including a fluorescent substance, and detecting the fluorescence (typically, the light in a range of the near-infrared region to the infrared region) generated from the sample will be illustrated by way of example. In this case, the optical characteristics to be measured typically include a spectrum and the quantum efficiency of the fluorescence generated from the sample.

Light source 4 generates the excitation light applied to the sample. A xenon discharge lamp (Xe lamp), a laser diode, a white LED (Light Emitting Diode) or the like is, for example, used as light source 4. In the case of measuring the quantum efficiency of the sample, the monochromatic light having a single wavelength corresponding to the characteristics of the sample is preferably used as the excitation light. In the case where the generated excitation light has an extent in the wavelength band (e.g., in the case of using a white light source such as a xenon discharge lamp), a wavelength band transmission filter for selecting the target monochromatic light may be provided.

In optical characteristic measurement system 1, a hemispheric integrating sphere is used as integrator 6. A spherical integrating sphere may also be used as integrator 6. By using the hemispheric integrating sphere, the measurement accuracy can be increased and the sample can be attached and detached more easily.

FIG. 2A shows one example of a measurement method in the case of measuring a powder sample or a solid sample, and FIG. 2B shows one example of a measurement method in the case of measuring a solution sample.

Referring to FIG. 2A, integrator 6 forms a hemispheric integration space therein. More specifically, integrator 6 includes a hemispheric portion 61 and a disc-shaped plane mirror 62 arranged to pass through a substantial curvature center of hemispheric portion 61 and close an opening of hemispheric portion 61. An inner surface (inner wall) of hemispheric portion 61 is provided with a light diffuse reflection layer 61a. Light diffuse reflection layer 61a is typically formed by applying or spraying a light diffusion material such as barium sulfate or PTFE (polytetrafluoroethylene). On the inner surface side of hemispheric portion 61, plane mirror 62 has a mirror-reflecting (regular-reflecting and diffuse-reflecting) light diffuse reflection layer 62a. Since light diffuse reflection layer 62a of plane mirror 62 is arranged to face the inside of hemispheric portion 61, a virtual image of hemispheric portion 61 is formed. By combining the space (real image) defined within hemispheric portion 61 and the virtual image formed by plane mirror 62, the same illuminance distribution as an illuminance distribution in the case of using the spherical integrator can be obtained.

A sample SMP1, which is a powder sample or a solid sample, is attached to a sample window 65 formed in a region including the apex of hemispheric portion 61. Sample SMP1 is attached to sample window 65 such that a fluorescent substance thereof is exposed to the inside of hemispheric portion 61.

The excitation light generated from light source 4 propagates through an optical fiber 5, passes through a light projecting optical system 50, and is applied to sample SMP1 arranged in integrator 6. Light projecting optical system 50 includes a collective lens 52 and collects the excitation light from light source 4 on sample SMP1. A light projecting window 64 for guiding the excitation light into integrator 6 is formed in plane mirror 62.

The light (typically, the fluorescence) generated from sample SMP1 having received the excitation light is repeatedly reflected inside integrator 6, and thus, the illuminance appearing on the inner surface of integrator 6 becomes uniform.

An observation window 67 for observing the illuminance on the inner surface of integrator 6 is formed in plane mirror 62, and a light extraction portion 68 is provided to correspond to observation window 67. An end of an optical fiber 7 optically connected to measurement apparatus 100 is connected to light extraction portion 68. Namely, the light having an intensity corresponding to the illuminance on the inner surface (corresponding to a range of a field of view when seen from observation window 67) of integrator 6 enters measurement apparatus 100. Based on the light observed through optical fiber 7, measurement apparatus 100 measures the optical characteristics of sample SMP1 and the like.

As shown in FIG. 2A, the user may simply attach sample SMP1 to sample window 65 provided at the apex (the lowermost portion in the figure) of hemispheric portion 61, and thus, the work for attaching and replacing the sample can be simplified even when measurement of a plurality of samples SMP1 is required.

Referring to FIG. 2B, in the case of measuring a sample SMP2 which is a solution sample, a sample holder 63 is attached to a sample window 66 formed in a central portion of plane mirror 62, and sample SMP2 is arranged in sample holder 63. At this time, a standard reflection member 69 is attached to sample window 65 formed in a region including the apex of hemispheric portion 61.

Light projecting optical system 50 is arranged at a position of extension of sample holder 63 in the length direction so as to correspond to sample window 66. Light projecting optical system 50 applies the excitation light from light source 4 to sample SMP2 through the inside of sample holder 63. The light (typically, the fluorescence) generated from sample SMP2 having received the excitation light is repeatedly reflected in integrator 6, and thus, the illuminance appearing on the inner surface of integrator 6 becomes uniform. Based on the light observed through optical fiber 7, measurement apparatus 100 measures the optical characteristics of sample SMP2 and the like with the method similar to the method in FIG. 2A.

In the use state shown in FIG. 2B, a standard reflection member is also attached to light projecting window 64 (not shown, refer to FIG. 2A).

Depending on a material, characteristics or the like of the sample, the re-excitation fluorescence may occur. The re-excitation fluorescence is a phenomenon in which the excitation light reflected by the surface of the sample is diffused and reflected in integrator 6, and thereafter, enters the sample again and further light emission occurs. In optical characteristic measurement system 1, an error caused by such re-excitation fluorescence can also be corrected.

Referring again to FIG. 1, measurement apparatus 100 receives the light observed through optical fiber 7, and outputs a measurement result (such as a spectrum). Data processing apparatus 200 processes the measurement result from measurement apparatus 100 to calculate the optical characteristics of the sample. The details of measurement apparatus 100 will be described below.

Figure 3:
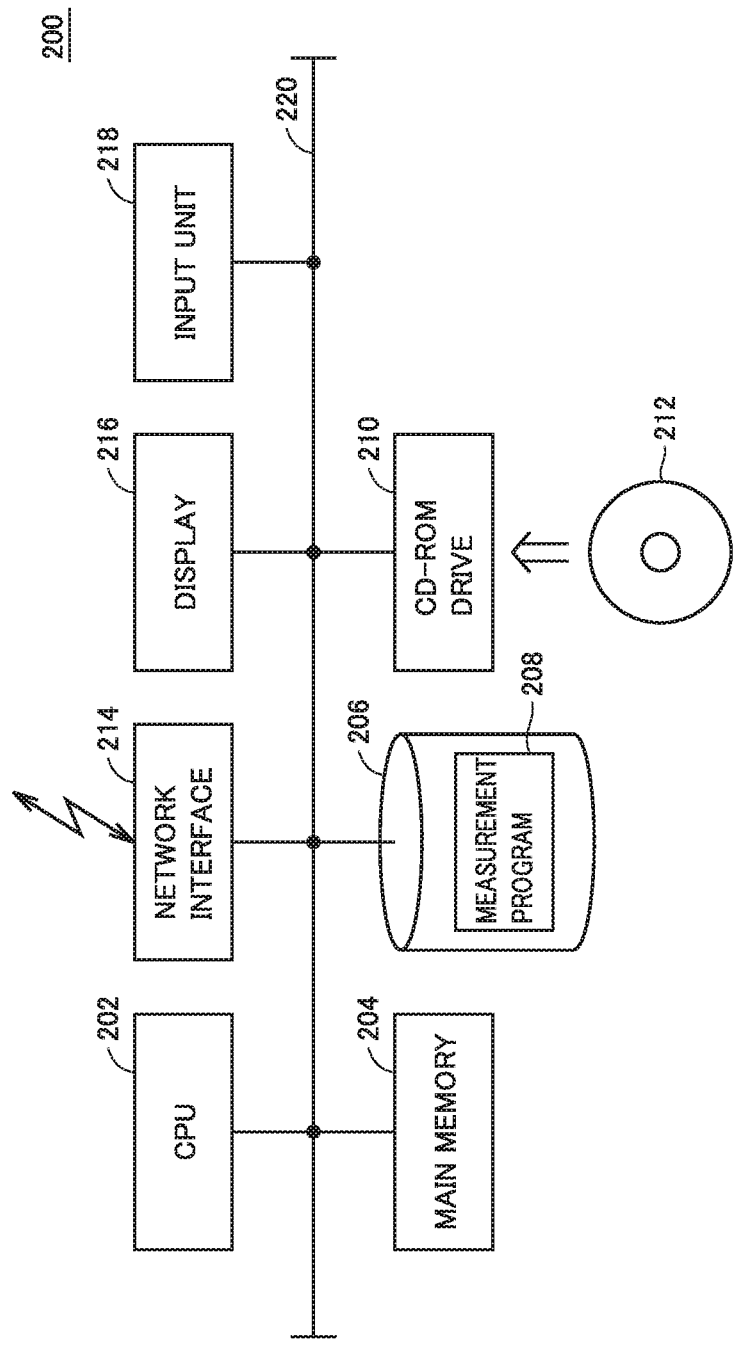
FIG. 3 is a schematic view showing an apparatus configuration of a data processing apparatus forming the optical characteristic measurement system shown in FIG. 1.

Data processing apparatus 200 is typically implemented by a general-purpose computer. FIG. 3 is a schematic view showing an apparatus configuration of data processing apparatus 200 forming optical characteristic measurement system 1 shown in FIG. 1. Data processing apparatus 200 includes a CPU (Central Processing Unit) 202 for executing various programs including the operating system (OS), a main memory 204 for temporarily storing data necessary for execution of the programs by CPU 202, and a hard disk 206 for storing in a non-volatile manner a measurement program 208 executed by CPU 202. The components forming measurement apparatus 100 are connected by a bus 220 so as to allow mutual communication.

Measurement program 208 for implementing the measurement method according to the present embodiment is prestored in hard disk 206. Such measurement program 208 is read by a CD-ROM (Compact Disk-Read Only Memory) drive 210 from a CD-ROM 212 or the like which is one example of a recording medium. Namely, measurement program 208 for implementing the measurement method according to the present embodiment is stored in the recording medium or the like such as CD-ROM 212 and is distributed. Alternatively, measurement program 208 may be distributed via the network. In such a case, measurement program 208 is received via a network interface 214 of data processing apparatus 200 and is stored in hard disk 206.

A display 216 shows the measurement result and the like to the user. An input unit 218 typically includes a keyboard, a mouse and the like, and accepts the user's operation.

A part or all of the functions described above may be implemented by a dedicated hardware circuit. In addition, data processing apparatus 200 may be incorporated as a part of system main body 2.

<B. Discovery of New Problem>

The case of applying the excitation light having a wavelength component in the ultraviolet region or the visible region to the sample and measuring the light generated from the sample is assumed, for example. In such measurement, the light generated from the sample is in many cases the very feeble light having a wavelength component in a range of the near-infrared region to the infrared region. In addition, the lifetime of some samples is short and thus only a small amount of measurement time can be secured.

Therefore, the use of a measurement apparatus having a highest possible detection sensitivity is preferable. There is also known a method for increasing the detection sensitivity by cooling the detection element with liquid nitrogen and the like as in the prior art. However, this method has such a problem that it takes a long time to perform a setup and handling is not easy.

Thus, by realizing the measurement apparatus with a detection element that can be used at an ordinary temperature without special cooling with liquid nitrogen and the like, the convenience of measurement is enhanced. In order to avoid a temperature-induced disturbance, the aforementioned detection element used at an ordinary temperature is provided with a function for keeping the temperature of the detection element itself constant.

The inventors of the present application have found such a new problem that when a detection gain of the detection element is increased in order to detect the very feeble light, measurement is affected by the ambient temperature of the measurement apparatus although the temperature of the detection element itself is kept constant. As a result of earnest study, the inventors of the present application have reached a conclusion that with variations in ambient temperature of the measurement apparatus, temperature variations occur in the measurement apparatus as well and the detection element having an increased gain also captures variations in radiant heat caused by the temperature variations, and as a result, the measurement result has an error caused by the variations although the intensity of light to be measured does not vary. Thus, the inventors of the present application have invented measurement apparatus 100 in which a function not causing the influence of the temperature variations occurring in the measurement apparatus, i.e., the influence of the radiant heat is newly adopted in addition to the detection element itself. In measurement apparatus 100 according to the present embodiment, stable measurement is possible even when the ambient temperature of measurement apparatus 100 varies.

<C. Configuration Example of Measurement Apparatus 100>

Next, a configuration example of measurement apparatus 100 according to the present embodiment will be described.

Figure 4:
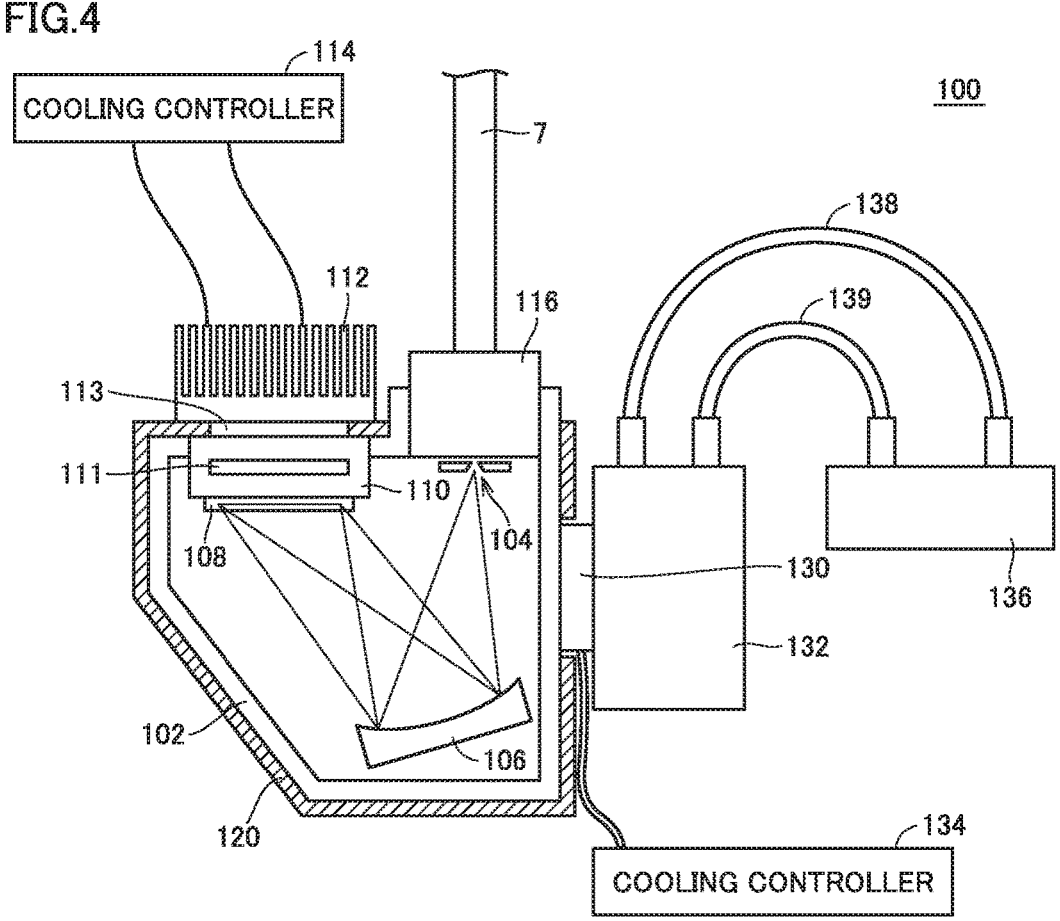
FIG. 4 is a schematic view showing an apparatus configuration of the measurement apparatus forming the optical characteristic measurement system shown in FIG. 1.

FIG. 4 is a schematic view showing an apparatus configuration of measurement apparatus 100 forming optical characteristic measurement system 1 shown in FIG. 1. Referring to FIG. 4, measurement apparatus 100 is a spectral photodetector, and includes an optical slit 104, a concave diffraction grating 106 and a detection element 108. These components are arranged in a housing 102.

A part of housing 102 is provided with a connection member 116 for attaching the end of optical fiber 7. By connection member 116, an optical axis at an opening end of optical fiber 7 is aligned with a central axis of optical slit 104. The light (hereinafter also referred to as "light to be measured") extracted from integrator 6 propagates through optical fiber 7 and passes through optical slit 104 of measurement apparatus 100. A cross-sectional diameter of the light to be measured is adjusted in optical slit 104 and the light to be measured enters concave diffraction grating 106.

The light to be measured enters concave diffraction grating 106, and thereby, the respective wavelength components included in the light to be measured are optically separated. Namely, the light to be measured is diffracted by concave diffraction grating 106, and thereby, the respective wavelength components included in the light to be measured travel in different directions corresponding to the wavelengths of the respective wavelength components. The respective wavelength components enter detection element 108 optically aligned with concave diffraction grating 106. Concave diffraction grating 106 is arranged to correspond to detection element 108 and is configured to guide the light in a prescribed wavelength range (the near-infrared region to the infrared region in this configuration example) to detection element 108.

An array sensor formed by arranging a plurality of independent detection surfaces side by side is used as detection element 108. A CCD (Charge-Coupled Device) image sensor may be used as detection element 108. The number and length of the detection surfaces forming detection element 108 are designed depending on the diffraction characteristics of concave diffraction grating 106 and the wavelength width to be detected. For every prescribed wavelength width, detection element 108 which is an array sensor detects an intensity spectrum of the light to be measured.

Detection element 108 has a self-cooling function at least partially joined to detection element 108, for cooling detection element 108. Detection element 108 is a self-cooling type detection element and is configured to increase the detection sensitivity and increase an S/N (Signal to Noise) ratio by reducing thermal noise and reducing a dark current. Specifically, detection element 108 has a base 110 having a cooling function. The function for cooling detection element 108 is mounted in base 110. Typically, an electronic cooling element 111 such as a Peltier element may be provided in base 110.

A cooling fin 112 is joined to a side of base 110 opposite to detection element 108, with a joining layer 113 interposed therebetween. A part of the heat generated at detection element 108 is absorbed by electronic cooling element 111 in base 110, and another part is transferred from cooling fin 112 to outside measurement apparatus 100 through base 110 and joining layer 113.

In electronic cooling element 111 of base 110, a current value and the like are controlled by a cooling controller 114. Based on a detection value from a not-shown temperature sensor and the like, cooling controller 114 controls the current value and the like such that the temperature of detection element 108 is maintained at a predetermined temperature.

In addition to the function for cooling detection element 108 itself, measurement apparatus 100 according to the present embodiment has mounted therein the function that does not have an influence of the variations in radiant heat on detection element 108. Namely, measurement apparatus 100 has a function and configuration for suppressing temperature variations occurring around detection element 108 in housing 102. In the configuration example shown in FIG. 4, a temperature control function for keeping the temperature of the internal space of housing 102 constant and a heat insulation function for reducing the heat entry into housing 102 are combined.

The temperature control function is implemented by a cooling mechanism at least partially joined to housing 102, for transferring the heat in housing 102 to outside housing 102. More specifically, the temperature control function includes an electronic cooling element 130 arranged on a side surface of housing 102, and a heat dissipation plate 132 joined to electronic cooling element 130. Electronic cooling element 130 is formed of a Peltier element or the like, and a current value and the like are controlled by a cooling controller 134.

A flow path (not shown) through which a coolant (typically such as water or chlorofluorocarbon) flows is formed within heat dissipation plate 132. Heat dissipation plate 132 is coupled to a coolant circulation pump 136 through coolant paths 138 and 139. Coolant circulation pump 136 allows the coolant to circulate through coolant path 138, heat dissipation plate 132 and coolant path 139 in this order. When coolant circulation pump 136 is operated, a part of the heat in housing 102 is transferred through heat dissipation plate 132 to outside, and in addition, is thermally exchanged with the coolant at heat dissipation plate 132 and transferred to outside on the circulation path by coolant circulation pump 136. Namely, heat dissipation plate 132 and coolant circulation pump 136 promote cooling of the inside of housing 102 by electronic cooling element 130.

The configuration of allowing the coolant to circulate between coolant circulation pump 136 and heat dissipation plate 132 by coolant circulation pump 136 has been described by way of example as the temperature control function. However, instead of heat dissipation plate 132, the configuration with the cooling fin may be employed similarly to the self-cooling function of detection element 108.

The heat insulation function is implemented by a structure arranged around housing 102, for reducing the heat entry into housing 102 from around housing 102. More specifically, as the heat insulation function, a heat insulation member 120 is arranged on an outer perimeter of housing 102. Although a member made of an arbitrary material can be used as heat insulation member 120, a fiber-based heat insulation member such as glass wool and rock wool may, for example, be used. Alternatively, a foamed heat insulation member such as urethane foam and polystyrene foam may be used. By arranging such heat insulation member 120 on the outer perimeter of housing 102, the heat entry into housing 102 from around housing 102 can be reduced.

As described above, measurement apparatus 100 according to the present embodiment has the function and configuration that do not have an influence of the variations in radiant heat by suppressing the temperature variations occurring around detection element 108. As long as the temperature variations occurring around detection element 108 is suppressed, measurement apparatus 100 is not limited to the configuration example shown in FIG. 4 and any configurations may be used.

For example, FIG. 4 shows the configuration example including the combination of the temperature control function implemented mainly by electronic cooling element 130 and the heat insulation function implemented mainly by heat insulation member 120. However, only one of these functions may be used.

As another configuration example, instead of heat insulation member 120, a vacuum layer may be provided on the outer perimeter side or on the inner perimeter side of housing 102 to reduce the heat entry from around housing 102. Alternatively, a temperature-controlled coolant (typically such as dry air and nitrogen) may be circulated around housing 102 to keep the temperature in housing 102 constant.

Furthermore, two or more functions, of the plurality of functions described above, may be combined appropriately.

Based on the aforementioned new discovery by the inventors of the present application, in measurement apparatus 100 according to the present embodiment, the temperature in housing 102 having detection element 108 arranged therein is controlled and stabilized, and thus, the influence of radiant heat on detection element 108 can be reduced, the detection sensitivity can be increased, and the S/N ratio can be increased.

In addition to the function and configuration for suppressing the temperature variations occurring around detection element 108 in housing 102, a region that is not used for measurement, of the detection surfaces of detection element 108, may also be subjected to masking to increase the stability of dark output.

<D. Improvement Effect>

Figure 5:
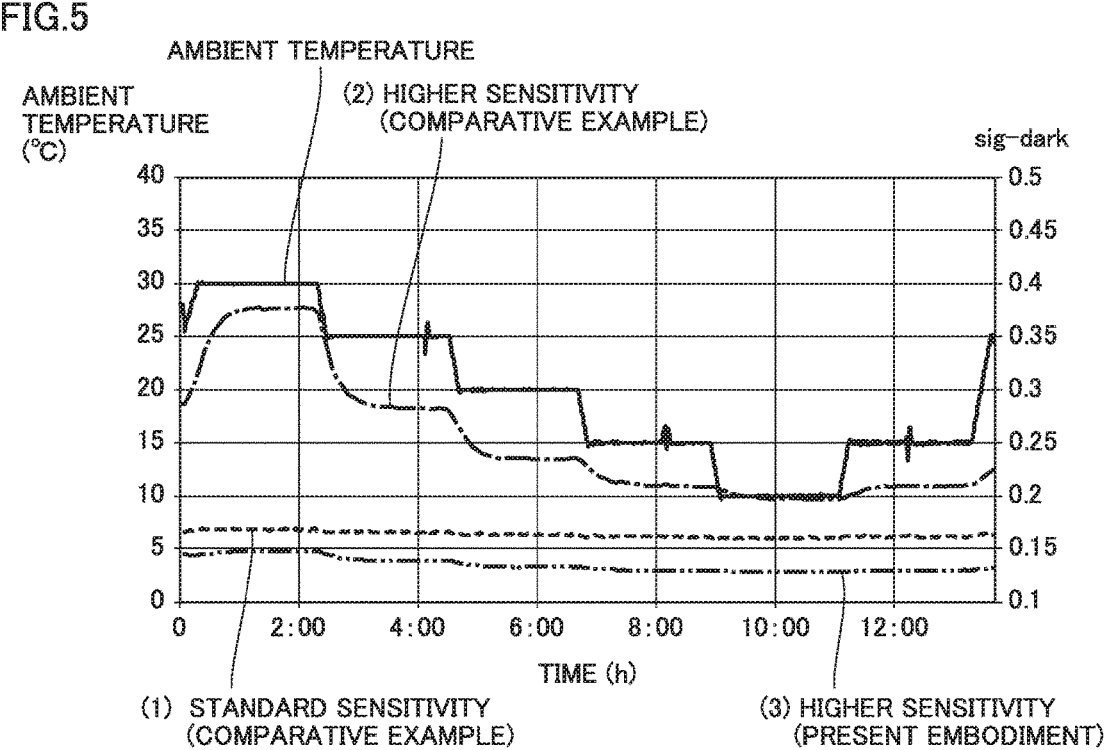
FIG. 5 is a graph showing a result of evaluation of an influence of a temperature drift in the measurement apparatus shown in FIG. 4.

Next, an improvement effect of a temperature drift in measurement apparatus 100 shown in FIG. 4 will be described. FIG. 5 is a graph showing a result of evaluation of an influence of the temperature drift in measurement apparatus 100 shown in FIG. 4. FIG. 5 shows a result of evaluation of variations in output value when measurement apparatus 100 shown in FIG. 4 is arranged in a thermostat bath and the ambient temperature is varied, and a result of evaluation of variations in output value when a measurement apparatus (Comparative Example) not including the temperature control function (electronic cooling element 130, heat dissipation plate 132, cooling controller 134, and coolant circulation pump 136) and the heat insulation function (heat insulation member 120) shown in FIG. 4 is arranged in the thermostat bath and the ambient temperature is varied.

"Ambient temperature" shown in FIG. 5 refers to temperature variations in the thermostat bath. Specifically, the ambient temperature was varied by 5° C. within the range of 10° C. to 30° C. in a stepwise manner every 2 hours.

As for the measurement apparatus of Comparative Example, measurement was performed in two types of states, i.e., in a state where the detection sensitivity of the detection element was set to be standard ("(1) standard sensitivity (Comparative Example)" in FIG. 5) and in a state where the detection sensitivity of the detection element was set to be higher ("(2) higher sensitivity (Comparative Example)" in FIG. 5). On the other hand, as for measurement apparatus 100 shown in FIG. 4, measurement was performed in a state where the detection sensitivity of the detection element was set to be higher ("(3) higher sensitivity (present embodiment)" in FIG. 5).

In either case, the output value after dark correction, with the incidence of the light to be measured being shut off, is shown. Each output value is a summed value obtained by repeating captures with an exposure time of 20 seconds four times. The measurement result shown in FIG. 5 is the output value after dark correction and a smaller value is more preferable.

As shown in FIG. 5, it can be seen that even the measurement apparatus of Comparative Example is affected a little by the variations in ambient temperature when the measurement apparatus of Comparative Example is used at the standard sensitivity. However, it can be seen that when the detection sensitivity is increased, the measurement apparatus of Comparative Example is affected by the variations in ambient temperature and the output value thereof varies even under the same measurement conditions.

In contrast, measures to reduce the heat entry into housing 102 from around housing 102 are taken in measurement apparatus 100 according to the present embodiment, and thus, measurement apparatus 100 according to the present embodiment is affected a little by the variations in ambient temperature, although the detection sensitivity is set to be higher. As a result, it can be seen that an influence of noise can be reduced as compared with the case of using the measurement apparatus of Comparative Example at the standard sensitivity.

<E. Configuration Suitable for Measurement of Quantum Efficiency>

Next, a configuration example suitable for measurement of the quantum efficiency will be described. For example, in the case of measuring the quantum efficiency of a sample including a fluorescent substance, it is necessary to apply the excitation light having a wavelength component in the ultraviolet region or the visible region to the sample, measure the applied excitation light, and in addition, measure the fluorescence having a wavelength component in the near-infrared region or the infrared region generated from the sample. Generally, the generated fluorescence is very feeble as compared with the excitation light. Furthermore, the lifetime of some samples is short and thus only a small amount of measurement time can be secured.

In such a case, a configuration including a combination of a first measurement apparatus for measuring mainly the excitation light and a second measurement apparatus for measuring mainly the fluorescence may be used. An apparatus configuration suitable for measurement of the quantum efficiency of the fluorescent substance will be described below by way of example.

Figure 6:
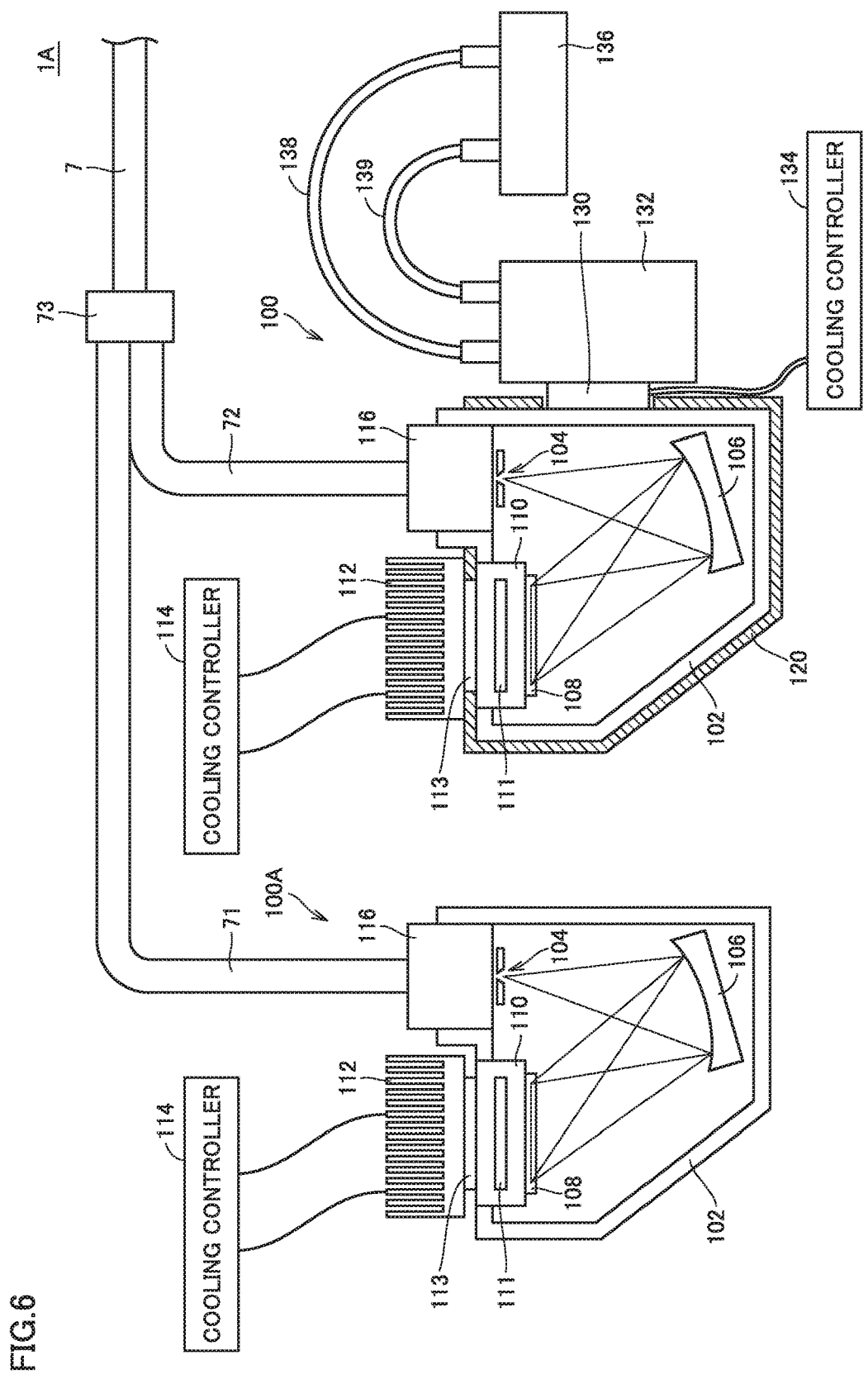
FIG. 6 is a schematic view showing a main portion of an apparatus configuration of an optical characteristic measurement system suitable for measurement of the quantum efficiency.

FIG. 6 is a schematic view showing a main portion of an apparatus configuration of an optical characteristic measurement system 1A suitable for measurement of the quantum efficiency. Referring to FIG. 6, optical characteristic measurement system 1A includes a measurement apparatus 100A for measuring mainly the excitation light, and measurement apparatus 100 for measuring mainly the fluorescence.

Optical characteristic measurement system 1A includes a bifurcated fiber for bifurcating the light from an object to be measured and guiding the light to each of measurement apparatus 100 and measurement apparatus 100A. Namely, at a bifurcation portion 73, optical fiber 7 connected to light extraction portion 68 of integrator 6 bifurcates into an optical fiber 71 connected to measurement apparatus 100A and an optical fiber 72 connected to measurement apparatus 100. Namely, the light observed through optical fiber 7 is divided into two lights and the two lights enter measurement apparatus 100 and measurement apparatus 100A, respectively.

Measurement apparatus 100A is for measuring mainly the excitation light and is designed such that a detection range is from the ultraviolet region to the visible region. On the other hand, measurement apparatus 100 is for measuring mainly the fluorescence and is designed such that a detection range is from the near-infrared region to the infrared region. Namely, measurement apparatus 100 is mainly configured to have a detection sensitivity to a wavelength component in the near-infrared region or the infrared region, and measurement apparatus 100A is configured to have a detection sensitivity to at least a part of wavelength components included in the range of the ultraviolet region to the visible region.

The apparatus configuration of measurement apparatus 100 is similar to the above-described apparatus configuration shown in FIG. 4. On the other hand, the apparatus configuration similar to the above-described apparatus configuration shown in FIG. 4 may be used as the apparatus configuration of measurement apparatus 100A. However, in the case of measuring the excitation light, the intensity of the light to be detected is higher, and thus, the temperature control function (electronic cooling element 130, heat dissipation plate 132, cooling controller 134, and coolant circulation pump 136) and the heat insulation function shown in FIG. 4 do not necessarily need to be provided. In optical characteristic measurement system 1A shown in FIG. 6, measurement apparatus 100A not including the temperature control function and the heat insulation function is used.

Because of the difference in detection range between measurement apparatus 100 and measurement apparatus 100A, concave diffraction grating 106 of measurement apparatus 100 is configured to guide the light in a prescribed wavelength range (the near-infrared region to the infrared region in this configuration example) to detection element 108, while concave diffraction grating 106 of measurement apparatus 100A is configured to guide the light in a different wavelength range (the ultraviolet region to the visible region in this configuration example) to detection element 108.

In addition, the detection sensitivity of detection element 108 of measurement apparatus 100 is set to be higher than the detection sensitivity of detection element 108 of measurement apparatus 100A. In other words, measurement apparatus 100A is configured to have the detection sensitivity lower than the detection sensitivity of measurement apparatus 100.

According to optical characteristic measurement system 1A shown in FIG. 6, the two measurement apparatuses can perform measurement in parallel, and thus, the spectrum in the range of the ultraviolet region to the near-infrared region (or the infrared region) can be measured simultaneously. For example, as a function for measuring the spectrum from the ultraviolet region to the near-infrared region (or the infrared region) with any measurement apparatus, there is known a configuration of mechanically rotating a diffraction grating sequentially to sequentially change a wavelength to be detected (i.e., sweep the wavelength). However, when such a function is used, there is a problem that it takes a relatively long time to complete the measurement of the target spectrum. There is also a problem that at the time of shift to the measurement in the near-infrared region or the infrared region after completion of the measurement in the ultraviolet region and the visible region, the mechanical switching operation is required, which may cause the measurement instability.

In order to deal with these problems, optical characteristic measurement system 1A shown in FIG. 6 has an array sensor (detection element 108 of measurement apparatus 100A) that can measure wavelengths in the range of the ultraviolet region to the visible region at a time, and an array sensor (detection element 108 of measurement apparatus 100) that can measure wavelengths in the range of the near-infrared region to the infrared region at a time. With such a configuration, the spectrum over the wide wavelength range can be measured simultaneously and in a short time, without sweeping the wavelength. In addition, by optimizing the detection sensitivity of detection element 108 of measurement apparatus 100A for measuring the excitation light having a high emission intensity and the detection sensitivity of detection element 108 of measurement apparatus 100 for measuring the fluorescence having a low emission intensity, it is possible to realize reasonable and economical optical characteristic measurement system 1A that can measure the quantum efficiency with a high degree of accuracy.

<F. Measurement Method>

Next, a measurement method with measurement apparatus 100 shown in FIG. 4 will be described. Similarly to optical characteristic measurement system 1A shown in FIG. 6, measurement can also be performed in accordance with the similar procedure in the case of using measurement apparatus 100 and measurement apparatus 100A.

Figure 7:
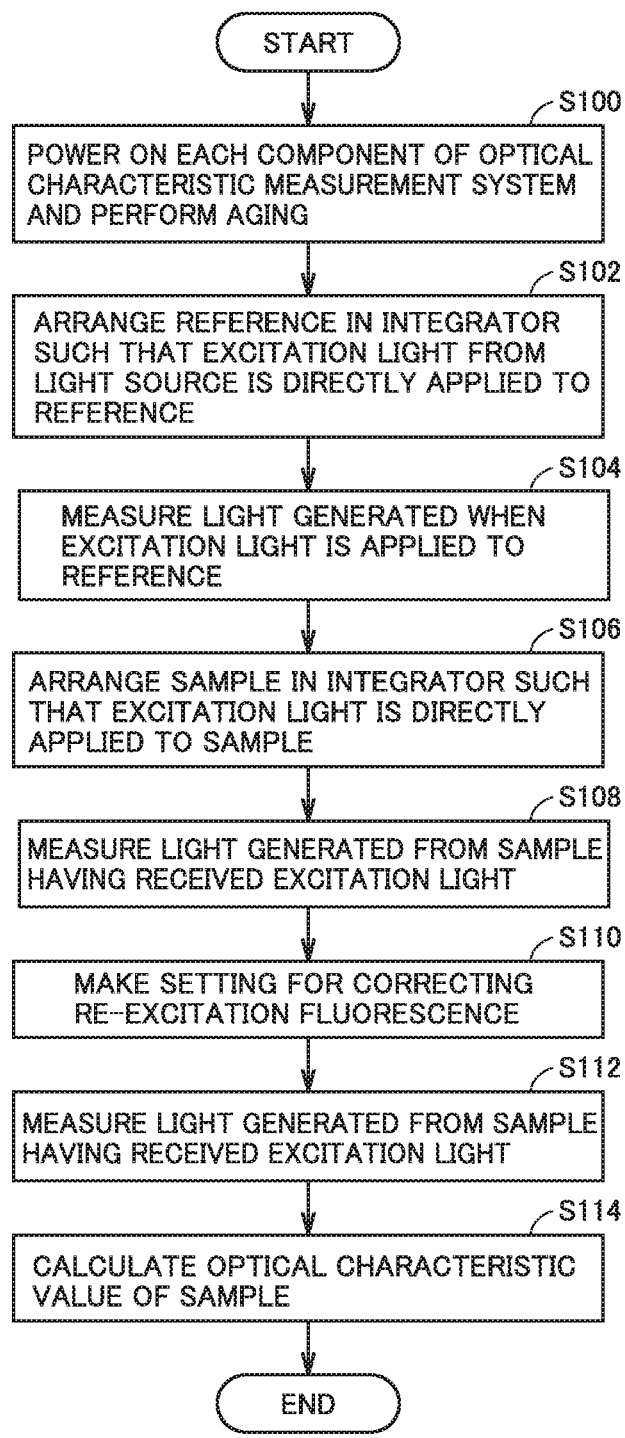
FIG. 7 is a flowchart showing a procedure of the measurement method with the measurement apparatus according to the present embodiment.

FIG. 7 is a flowchart showing a procedure of the measurement method with measurement apparatus 100 according to the present embodiment. Referring to FIG. 7, the user first powers on each component of the optical characteristic measurement system and performs aging (step S100). Specifically, aging includes stabilization of the self-cooling function of detection element 108 forming measurement apparatus 100, stabilization of the temperature in housing 102 of measurement apparatus 100, stabilization of light source 4, and the like.

The user arranges a reference in integrator 6 such that the excitation light from light source 4 is directly applied to the reference (step S102). In the case of a powder sample or a solid sample, standard reflection member 69 (see FIG. 2B) serves as the reference. In the case of a solution sample, only a solvent contained in a container of the same type as that of a container containing the sample serves as the reference. Measurement apparatus 100 measures the light when the excitation light is applied to the reference (step S104). This measurement value is a value indicating an influence of light absorption and the like that occur during measurement of the sample, and is used as a correction value.

Then, the user arranges a sample in integrator 6 such that the excitation light from light source 4 is directly applied to the sample (step S106). Measurement apparatus 100 measures the light generated from the sample having received the excitation light (step S108). At this time, measurement apparatus 100 measures the excitation light having passed through the sample and/or the excitation light having been reflected by the sample, in addition to the light generated from the sample.

Then, the user makes a setting for correcting the re-excitation fluorescence (step S110). Measurement apparatus 100 measures the light generated from the sample having received the excitation light (step S112). As the setting for correcting the re-excitation fluorescence, in the case of a powder sample or a solid sample, the sample is arranged at a position where the excitation light from light source 4 is not directly applied, and the light generated when the excitation light reflected in integrator 6 is applied to the sample is measured. In the case of a solution sample, measurement is performed in a state where standard reflection member 69 attached to sample window 65 of integrator 6 is removed such that the excitation light having passed through the sample is not reflected in integrator 6.

Finally, by using the result of measurement by measurement apparatus 100 in step S104, the result of measurement by measurement apparatus 100 in step S108, and the result of measurement by measurement apparatus 100 in step S112, data processing apparatus 200 calculates an optical characteristic value (such as, for example, the quantum efficiency) of the sample (step S114).

<G. Measurement Result Example>

Figure 8A:
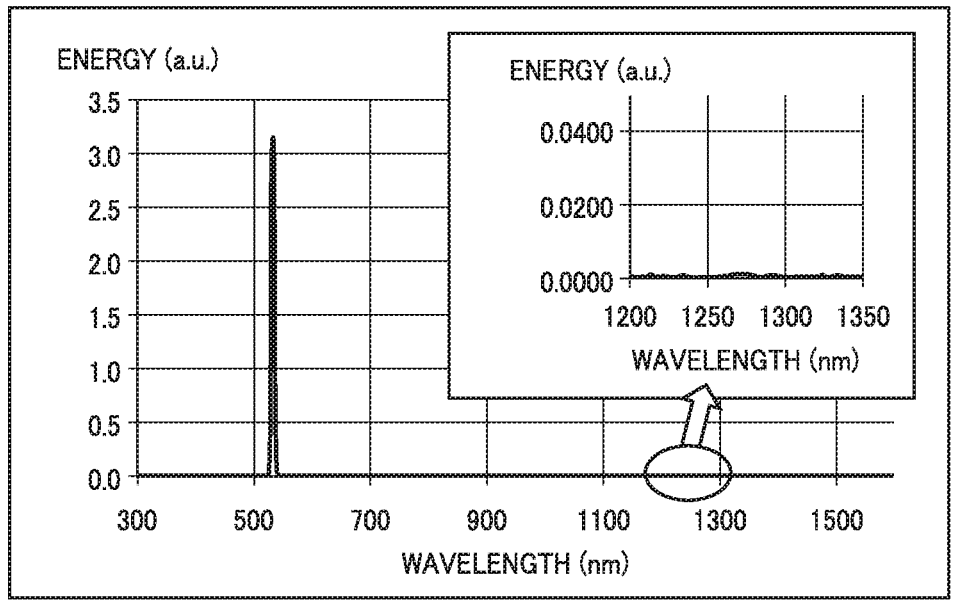
FIGS. 8A and 8B are diagrams showing an example of a measurement result when singlet oxygen is generated from fullerene ($C_{60}$) in a solvent with the optical characteristic measurement system shown in FIG. 6.
Figure 8B:
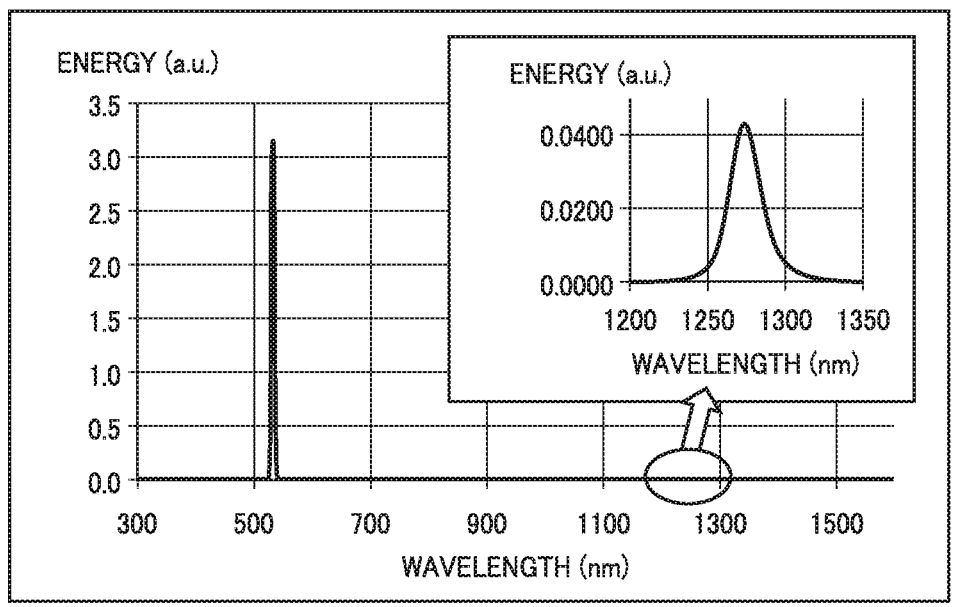

Next, one example of the result of measurement of the sample with optical characteristic measurement system 1A shown in FIG. 6 will be described. FIGS. 8A and 8B show an example of a measurement result when singlet oxygen is generated from fullerene ($C_{60}$) in a solvent with optical characteristic measurement system 1A shown in FIG. 6. FIG. 8A shows, as Comparative Example, an example of using the measurement apparatus including the detection element whose detection sensitivity is set to be standard. FIG. 8B shows an example of employing the configuration shown in FIG. 4 and using the measurement apparatus including the detection element whose detection sensitivity is set to be higher.

More specifically, the excitation light was applied to fullerene existing in a solvent of deuterated benzene ($C_6D_6$), to generate singlet oxygen. FIG. 8 shows one example of a result of measurement of a spectrum of the fluorescence generated in the process of generating singlet oxygen. A 532 nm laser light source (output: 20 mW) was used as light source 4 for generating the excitation light.

As shown in FIG. 8A, it can be seen that the spectrum of the generated fluorescence cannot be measured when the detection sensitivity of the detection element is set to be standard. On the other hand, as shown in FIG. 8B, it can be seen that the spectrum of the generated fluorescence can be measured when the detection sensitivity of the detection element is set to be higher.

Furthermore, by using optical characteristic measurement system 1A shown in FIG. 6, the internal quantum efficiency of fullerene in the solvent was measured. Correction of the re-excitation fluorescence was also performed. In order to study the measurement stability, the same measurement was repeatedly performed on the same sample for 3 days (the measurement was performed once a day and three times in total). The result is shown below.

First day: 0.061%
Second day: 0.062%
Third day: 0.062%

According to this result of measurement of the quantum efficiency, it can be seen that the quantum efficiency can be measured in a stable manner even in the case of the sample having very low quantum efficiency.

<H. Calibration Method>

Optical characteristic measurement system 1A shown in FIG. 6 includes two measurement apparatuses 100 and 100A having different detection sensitivities. With consideration given to measurement of the quantum efficiency and the like, energy calibration using the same standard light source is required. That is to say, matching the size of energy converted from the measurement value is required between the two measurement apparatuses. On the other hand, since the two measurement apparatuses have different detection sensitivities, energy calibration about the two measurement apparatuses using the same standard light source is not easy. Thus, one example of a calibration method for measurement apparatuses 100 and 100A forming optical characteristic measurement system 1A according to the present embodiment will be described.

Figure 10A:
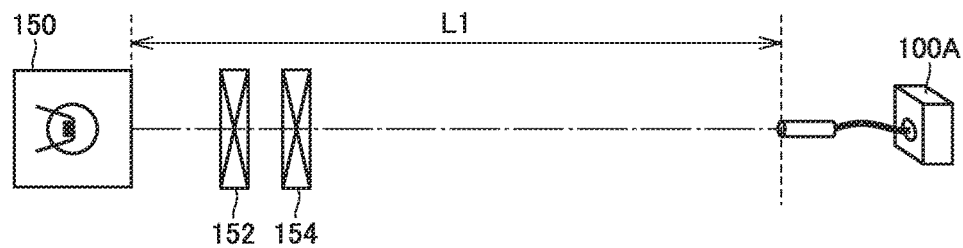
FIGS. 10A to 10C are schematic views for describing a procedure for performing calibration on the optical characteristic measurement system according to the present embodiment.
Figure 10B:
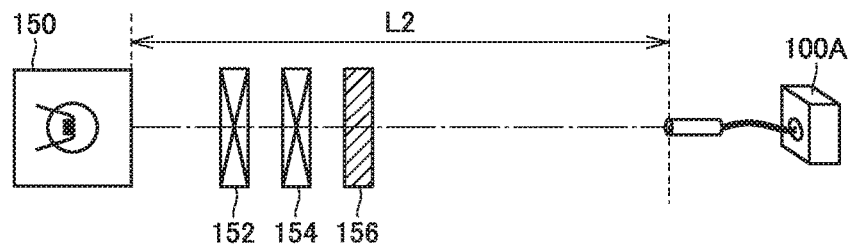
Figure 10C:
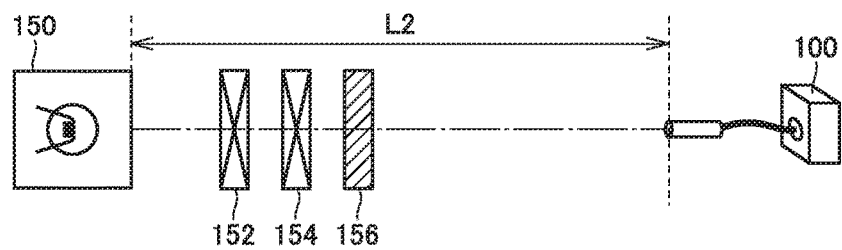

FIG. 9 is a flowchart showing a procedure for performing calibration on optical characteristic measurement system 1A according to the present embodiment. FIGS. 10A to 10C are schematic views for describing the procedure for performing calibration on optical characteristic measurement system 1A according to the present embodiment.

Referring to FIGS. 9 and 10A to 10C, a standard lamp 150 used for calibration is first valued by an illumination and the like at a distance L1 with a preliminarily calibrated higher-order standard light source (an international standard traceable light source) (step S200). A 50 W light source is, for example, used as standard lamp 150. By step S200, an energy value for standard lamp 150 is obtained. The energy value is typically defined by using a spectral irradiance [$\mu W\ cm^{-2}\ nm^{-1}$].

Then, standard lamp 150 which is a light source preliminarily valued by the energy value and measurement apparatus 100A are arranged in accordance with a prescribed arrangement condition. By way of example, as shown in FIG. 10A, standard lamp 150 and measurement apparatus 100A (standard sensitivity) are arranged, with optical axes thereof being matched with each other and with standard lamp 150 and measurement apparatus 100A being spaced apart from each other by distance L1 (step S202). In order to reduce an influence of a stray light component and the like generated from standard lamp 150, baffle units 152 and 154 are arranged between standard lamp 150 and measurement apparatus 100A.

An energy calibration coefficient of measurement apparatus 100A is determined based on an output value obtained by receiving the light from standard lamp 150 at measurement apparatus 100A. Namely, the energy calibration coefficient of measurement apparatus 100A is calculated based on the output value from measurement apparatus 100A under the arrangement condition shown in FIG. 10A (step S204).

The energy calibration coefficient is a coefficient for converting the output value (signal value) from the measurement apparatus into energy, and has a relationship of energy=output value after dark correction (measurement value−measurement value at the time of dark correction)/energy calibration coefficient.

In step S204, the energy calibration coefficient is calculated by subtracting a dark correction value (a measurement value Id2 output in a dark state) of measurement apparatus 100A from a measurement value I2 of measurement apparatus 100A to obtain a value, and dividing this value by the energy value valued to standard lamp 150. Namely, an energy calibration coefficient k2 of measurement apparatus 100A=(I2−Id2)/(an energy value E1 valued to standard lamp 150).

Then, standard lamp 150 which is a light source and measurement apparatus 100A are arranged in accordance with a different arrangement condition. By way of example, as shown in FIG. 10B, the distance between standard lamp 150 and measurement apparatus 100A (standard sensitivity) is reduced from distance L1 to a distance L2, and a light attenuating mesh 156 is arranged on the optical axis between standard lamp 150 and measurement apparatus 100A (step S206). A light attenuating mesh having a transmittance of 1% (i.e., light attenuation to 1/100) can, for example, be used as light attenuating mesh 156. A reason why the distance is reduced from distance L1 to distance L2 is to reduce the degree of light attenuation by light attenuating mesh 156, and changing the distance is not necessary if more appropriate light attenuating mesh 156 can be prepared.

A converted energy value of standard lamp 150 corresponding to the current arrangement condition is determined based on the output value obtained by receiving the light from standard lamp 150 at measurement apparatus 100A and the energy calibration coefficient of measurement apparatus 100A. Namely, the converted energy value of standard lamp 150 reflecting light attenuating mesh 156 and distance L2 is calculated based on the output value from measurement apparatus 100A under the arrangement condition shown in FIG. 10B (step S208). Specifically, a converted energy value E2 is calculated by subtracting the dark correction value (measurement value Id2 output in a dark state) of measurement apparatus 100A from a measurement value I2' of measurement apparatus 100A to obtain a value, and multiplying this value by energy calibration coefficient k2 calculated in step S204. Namely, converted energy value E2=(I2'−Id2)×energy calibration coefficient k2.

Then, standard lamp 150 which is a light source and measurement apparatus 100 are arranged in accordance with the different arrangement condition. By way of example, with the arrangement state of baffle units 152 and 154 and light attenuating mesh 156 being maintained in the state shown in FIG. 10B, measurement apparatus 100 (higher sensitivity) is arranged instead of measurement apparatus 100A (standard sensitivity) (see FIG. 10C) (step S210).

An energy calibration coefficient of measurement apparatus 100 is determined based on an output value obtained by receiving the light from standard lamp 150 at measurement apparatus 100 and the converted energy value of standard lamp 150 corresponding to the arrangement condition in FIG. 10B. Namely, the energy calibration coefficient of measurement apparatus 100 is calculated based on the output value from measurement apparatus 100 under the arrangement condition shown in FIG. 10C (step S212). In step S212, the energy calibration coefficient is calculated by subtracting the dark correction value (a measurement value Id1 output in a dark state) of measurement apparatus 100 from a measurement value I1 of measurement apparatus 100 to obtain a value, and dividing this value by converted energy value E2 calculated in step S208. Namely, an energy calibration coefficient k1 of measurement apparatus 100=(I1−Id1)/(converted energy value E2 of standard lamp 150).

In accordance with the procedure described above, the energy calibration coefficients of measurement apparatus 100 and measurement apparatus 100A can be determined with the same standard light source.

In accordance with the difference in sensitivity between measurement apparatus 100 (higher sensitivity) and measurement apparatus 100A (standard sensitivity), a wattage of standard lamp 150, a difference between distance L1 and distance L2, the characteristics of the light attenuating mesh, and the like may be adjusted appropriately.

<I. Advantages>

Measurement apparatus 100 according to the present embodiment has the function and configuration for suppressing the temperature variations occurring around detection element 108 in housing 102. With such function and configuration, measurement with reduced influence of measurement noise becomes possible even when the detection sensitivity of detection element 108 is increased. By using such measurement apparatus 100, the very feeble light generated from the sample when the excitation light having a wavelength component in the ultraviolet region or the visible region is applied to the sample can also be measured in a stable manner, for example.

In addition, in measurement apparatus 100 according to the present embodiment, the scheme for cooling detection element 108 itself and the inside of housing 102 with the electronic cooling element is employed. Therefore, the measurement time including aging can be significantly shortened as compared with the scheme for cooling with liquid nitrogen or the like.

In optical characteristic measurement system 1A according to the present embodiment, the light from the object to be measured can be simultaneously measured with measurement apparatus 100 and measurement apparatus 100A having different detection ranges. In both measurement apparatus 100 and measurement apparatus 100A, the array sensor (the CCD image sensor as one example) is used as the detection element, and measurement apparatus 100 and measurement apparatus 100A can obtain the intensity of a plurality of wavelength components at a time. As a result, the spectrum over the wide band can be measured with higher sensitivity. In addition, the measurement time can be shortened as compared with the wavelength sweeping scheme.

In addition, by optimizing the detection sensitivities of measurement apparatus 100 and measurement apparatus 100A, the very feeble light can be measured in a stable manner with a high degree of reproducibility, without being affected by variations in ambient environment. Therefore, the quantum efficiency can be measured with a high degree of accuracy. With such an apparatus configuration, the fluorescence having a wavelength component in the near-infrared region generated by a substance in a living body can, for example, be detected. In addition, the present invention is also applicable to the development of various materials. Furthermore, the present invention is also applicable to the field of energy development in which the synthesized artificial light is used.

From the description above, the remaining advantages related to the optical characteristic measurement apparatus and the optical characteristic measurement system according to the present embodiment will become clear.

While the embodiment of the present invention has been described, it should be understood that the embodiment disclosed herein is illustrative and non-restrictive in every respect. The scope of the present invention is defined by the terms of the claims, and is intended to include any modifications within the meaning and scope equivalent to the terms of the claims.

What is claimed is:

1. A calibration method for an optical characteristic measurement system including a first measurement apparatus and a second measurement apparatus configured to have a detection sensitivity lower than a detection sensitivity of the first measurement apparatus, the method comprising:

arranging a light source preliminarily valued by an energy value and the second measurement apparatus in accordance with a first arrangement condition, and determining an energy calibration coefficient of the second measurement apparatus based on an output value obtained by receiving light from the light source at the second measurement apparatus;

arranging the light source and the second measurement apparatus in accordance with a second arrangement condition, and determining a converted energy value of the light source corresponding to the second arrangement condition based on the output value obtained by receiving the light from the light source at the second measurement apparatus and the energy calibration coefficient of the second measurement apparatus; and arranging the light source and the first measurement apparatus in accordance with the second arrangement condition, and determining an energy calibration coefficient of the first measurement apparatus based on an output value obtained by receiving the light from the light source at the first measurement apparatus and the converted energy value of the light source corresponding to the second arrangement condition.

2. The calibration method according to claim 1, further comprising
attenuating intensity of the light from the light source.

3. The calibration method according to claim 2, wherein the step of attenuating intensity of the light from the light source comprises arranging a light attenuating mesh between the light source and the measurement apparatus.

4. The calibration method according to claim 1, wherein the second measurement apparatus is spaced from the light source by a first distance in the first arrangement condition, and
each of the first and second the second measurements is spaced from the light source by a second distance smaller than the second distance in the second arrangement condition.

5. The calibration method according to claim 1, wherein the light source is calibrated with a higher-order standard light source which is an international standard traceable light source.

* * * * *